United States Patent
Suyama et al.

(10) Patent No.: US 7,464,060 B2
(45) Date of Patent: Dec. 9, 2008

(54) TIME SERIES PATTERN EXTRACTION APPARATUS AND METHOD

(75) Inventors: Akihiro Suyama, Tokyo (JP); Ken Ueno, Kanagawa-ken (JP); Shigeaki Sakurai, Tokyo (JP); Ryohei Orihara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 432 days.

(21) Appl. No.: 11/239,422

(22) Filed: Sep. 30, 2005

(65) Prior Publication Data

US 2006/0129554 A1 Jun. 15, 2006

(30) Foreign Application Priority Data

Nov. 30, 2004 (JP) ............................. 2004-347585

(51) Int. Cl.
*G06F 15/18* (2006.01)

(52) U.S. Cl. ........................................................ 706/12

(58) Field of Classification Search ........................ None
See application file for complete search history.

(56) References Cited

U.S. PATENT DOCUMENTS

| | | | | |
|---|---|---|---|---|
| 4,802,224 A * | 1/1989 | Shiraki et al. | ................ | 704/245 |
| 5,673,366 A * | 9/1997 | Maynard et al. | ............... | 706/14 |
| 6,578,966 B2 * | 6/2003 | Fink et al. | .................... | 351/239 |
| 6,618,725 B1 * | 9/2003 | Fukuda et al. | .................. | 707/6 |
| 6,728,691 B1 * | 4/2004 | Neuneier et al. | ............... | 706/30 |
| 6,769,770 B2 * | 8/2004 | Fink et al. | .................... | 351/239 |
| 6,826,569 B2 * | 11/2004 | Robertson | ....................... | 707/6 |
| 7,101,044 B2 * | 9/2006 | Fink | ............................ | 351/211 |
| 7,155,390 B2 * | 12/2006 | Fukada | ........................ | 704/254 |

(Continued)

FOREIGN PATENT DOCUMENTS

JP 2004-213551 7/2004

(Continued)

OTHER PUBLICATIONS

Statistical Characteristics of Velocity of Movements of Limbs in Young Infants during the Conjugate Reinforcement Mobile Task Saji, R.; Watanbe, H,; Taga, G.; Development and Learning, 2005. Proceedings. The 4th International Conference on Jul. 19-21, 2005 pp. 203-206 digital Object Identifier 10.1109/DEVLRN.2005.1490984.*

(Continued)

*Primary Examiner*—Michael B Holmes
(74) *Attorney, Agent, or Firm*—Finnegan, Henderson, Farabow, Garrett & Dunner, L.L.P.

(57) ABSTRACT

A time series pattern generation unit extracts a key concept corresponding to a text of each data element of a plurality of time series data by referring to an extraction rule memory, and generates a plurality of time series patterns. A colony generation unit unifies a plurality of data elements having the same key concept and substantially the same time duration, and generates colonies of unified elements. In response to a selection of a first colony, a colony extraction unit specifies a second colony having a key concept contrary to the first colony, and extracts colonies earlier than the first colony and the second colony. A time reason extraction unit extracts a time reason as a divergence condition of the first colony from the second colony from the extracted colonies.

15 Claims, 6 Drawing Sheets

U.S. PATENT DOCUMENTS

| | | | |
|---|---|---|---|
| 7,326,980 B2 * | 2/2008 | Ahn et al. | 706/30 |
| 7,346,595 B2 * | 3/2008 | Aoyama et al. | 706/25 |
| 7,398,268 B2 * | 7/2008 | Kim et al. | 707/3 |
| 2004/0186835 A1 | 9/2004 | Sakurai | |

FOREIGN PATENT DOCUMENTS

| | | |
|---|---|---|
| JP | 2004-287798 | 10/2004 |

OTHER PUBLICATIONS

A periodic motion pattern generation by recalling well-suited CPG parameters based on time-series observations Kondo, T.; Somei, T.; Ito, K,; SICE 2004 Annual Conference vol. 3, Aug. 4-6, 2004 pp. 2171-2176 vol. 3.*

A predictive constraints selection model for periodic motion pattern generationKondo, T.; Somei, T.; Ito, K.; Intelligent Robots and Systems, 2004. (IROS 2004). Proceedings. 2004 IEEE/RSJ International Conference on vol. 1, Sep. 28-Oct. 2, 2004 pp. 975-980 vol. 1 Digital Object Identifier 10.1109/IROS.2004.1389479.*

Unsupervised Learning, Recognition, and Generation of Time-series Patterns based on Self-Organizing Segmentation Okada, S.; Hasegawa, O.; Robot and Human Interactive Communication, 2006. Roman 2006. The 15th IEEE International Symposium on Sep. 6-8, 2006 pp. 716-721 Digital Object Identifier 10.1109/ROMAN.2006. 314485.*

Binary prediction based on weighted sequential mining method Shuchuan Lo; Web Intelligence, 2005. Proceedings. The 2005 IEEE/WIC/ACM International Conference on Sep. 19-22, 2005 pp. 755-761 Digital Object identifier 10.1109/WI.2005.42.*

Sakurai, S., "Time Series Data Analysis Apparatus and Method," U.S. Appl. No. 11/100,512, filed Apr. 7, 2005.

* cited by examiner

TIME SERIES PATTERN 1

| PATTERN ELEMENT INDEX | KEY CONCEPT | DAYS PASSED FROM PREVIOUS PATTERN ELEMENT |
|---|---|---|
| 1 | GENERAL · REQUEST | MIN : 0<br>MAX : 0 |
| 2 | GENERAL · INQUIRY | MIN : 2<br>MAX : 4 |
| 3 | EXPLANATION · FUNCTION<br>EXPLANATION · MAINTENANCE | MIN : 2<br>MAX : 5 |
| 4 | RESULT · ACCEPTANCE OF AN ORDER | MIN : 2<br>MAX : 4 |

TIME SERIES PATTERN 2

| PATTERN ELEMENT INDEX | KEY CONCEPT | DAYS PASSED FROM PREVIOUS PATTERN ELEMENT |
|---|---|---|
| 1 | GENERAL · REQUEST | MIN : 0<br>MAX : 0 |
| 2 | GENERAL · INQUIRY | MIN : 2<br>MAX : 4 |
| 3 | EXPLANATION · FUNCTION<br>EXPLANATION · MAINTENANCE | MIN : 2<br>MAX : 3 |
| 4 | UNPOPULARITY · PRICE | MIN : 2<br>MAX : 2 |

TIME SERIES PATTERN 3

| PATTERN ELEMENT INDEX | KEY CONCEPT | DAYS PASSED FROM PREVIOUS PATTERN ELEMENT |
|---|---|---|
| 1 | GENERAL · REQUEST | MIN : 0<br>MAX : 0 |
| 2 | GENERAL · INQUIRY | MIN : 2<br>MAX : 4 |
| 3 | EXPLANATION · FUNCTION<br>EXPLANATION · MAINTENANCE | MIN : 6<br>MAX : 9 |
| 4 | RESULT · UNACCEPTANCE OF AN ORDER | MIN : 2<br>MAX : 4 |

TIME SERIES PATTERN EXTRACTION APPARATUS AND METHOD

CROSS-REFERENCE TO RELATED APPLICATIONS

This application is based upon and claims the benefit of priority from prior Japanese Patent Application No. 2004-347585, filed on Nov. 30, 2004; the entire contents of which are incorporated herein by reference.

FIELD OF THE INVENTION

The present invention relates to a time series pattern extraction apparatus and a method for extracting a time series pattern from data stored with passage of time.

BACKGROUND OF THE INVENTION

In numerical data or text data stored with passage of time, a time series rule is often included. In order to find the time series rule, a time series pattern extraction apparatus is provided. In the time series pattern extraction apparatus, a usable pattern is extracted from the numerical data or the text data, and presented to an analyst. Examples of numerical data or the text data stored with passage of time include a daily report mentioning sales data or business information in a retail region, a diary recording daily biological data (such as a blood pressure or a pulse), a personal behavior or feeling in a health control region, daily stock price data in a financial region, and news mentioned in a newspaper.

In the time series pattern extraction apparatus of the prior art (Japanese Patent Disclosure (Kokai) No. 2004-287798, pages 7 and 8, and FIG. 12), even if information element in the time series data is either a numerical value or a text, a time series pattern is extracted from the high frequency time series data. Furthermore, even if information element in the time series data is a combination of numerical values and text, the time series pattern is extracted from the high frequency time series data.

In the above-mentioned time series pattern extraction apparatus, a time event representing what time series pattern exists can be extracted from the time series data. However, a time reason why the time series pattern is generated cannot be extracted from the time series data. Accordingly, the analyst must find the time reason by examining a generation process of the time series pattern.

SUMMARY OF THE INVENTION

The present invention is directed to a time series pattern extraction apparatus and a method for extracting a time reason why the time series pattern is generated from the time series data.

According to an aspect of the present invention, there is provided an apparatus for extracting a time series pattern, comprising: a data memory storing a plurality of time series data, each data element including a time and a text; an extraction rule memory storing a correspondence relation between a key concept and a text expression; a time series pattern generation unit configured to extract key concepts corresponding to the text of each data element of the plurality of time series data from said extraction rule memory, and to generate a plurality of time series patterns from the plurality of time series data, each pattern including data elements each having a time and a key concept; a colony generation unit configured to unify a plurality of elements having the same key concepts and substantially the same time duration, and to generate colonies of unified data elements; a select unit selecting a first colony from the colonies, the first colony having a first key concept; a colony extraction unit configured to specify a second colony having a second key concept contrary to the first key concept, and to extract colonies each having a time earlier than the first colony and the second colony; and a time reason extraction unit configured to extract a time reason as a divergence condition of the first colony from the second colony from the extracted colonies.

According to another aspect of the present invention, there is also provided a method for extracting a time series pattern, comprising: storing a plurality of time series data, each data element including a time and a text in a data memory; storing a correspondence relation between a key concept and a text expression in an extraction rule memory; extracting key concepts corresponding to the text of each data element of the plurality of time series data from the extraction rule memory; generating a plurality of time series patterns from the plurality of time series data, each pattern including data elements each having a time and a key concept; unifying a plurality of data elements having the same key concept and substantially the same time duration; generating colonies of unified data elements unified; selecting a first colony from the colonies, the first colony having a first key concept; specifying a second colony having a second key concept contrary to the first colony; extracting colonies each having a time earlier than the first colony and the second colony; and extracting a time reason as a divergence condition of the first colony from the second colony from the extracted colonies.

According to still another aspect of the present invention, there is also provided a computer program product, comprising: a computer readable program code embodied in said product for causing a computer to extract a time series pattern, said computer readable program code comprising: a first program code to store a plurality of time series data, each data element including a time and a text in a data memory; a second program code to store a correspondence relation between a key concept and a text expression in an extraction rule memory; a third program code to extract key concepts corresponding to the text of each data element of the plurality of time series data from the extraction rule memory; a fourth program code to generate a plurality of time series pattern from the plurality of time series data, each pattern including elements each having a time and a key concept; a fifth program code to unify a plurality of data elements having the same key concept and substantially the same time duration; a sixth program code to generate colonies of unified data elements; a seventh program code to select a first colony from the colonies, the first colony having a first key concept; an eighth program code to specify a second colony having a second key concept contrary to the first key concept; a ninth program code to extract colonies each having a time earlier than the first colony and the second colony; and a tenth program code to extract a time reason as a divergence condition of the first colony from the second colony from the extracted colonies.

DETAILED DESCRIPTION OF THE EMBODIMENTS

Hereinafter, various embodiments of the present invention will be explained by referring to the drawings. The present invention is not limited to following embodiments.

Figure 1:
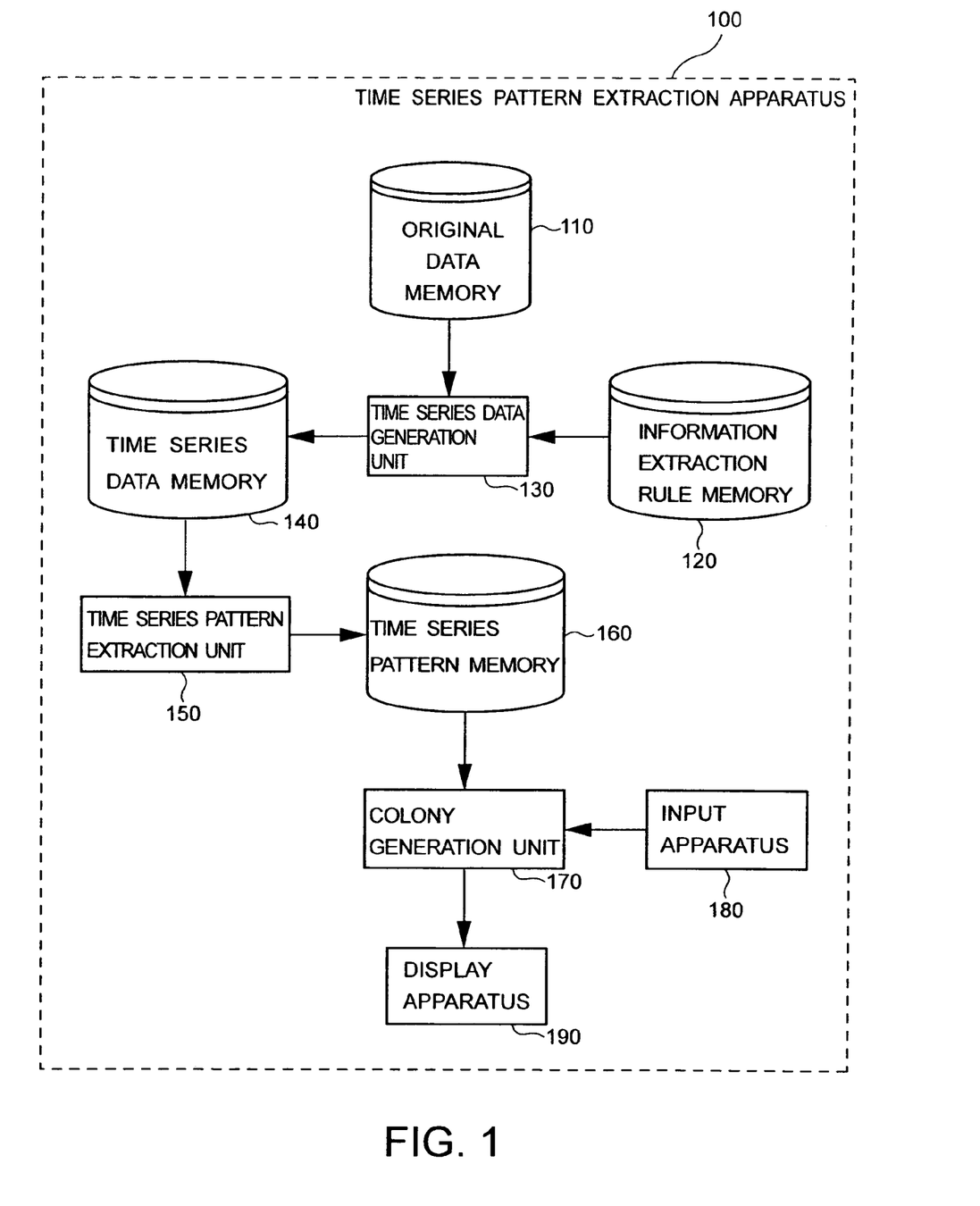
FIG. 1 is a block diagram of a time series pattern extraction apparatus according to a first embodiment.
Figure 2:
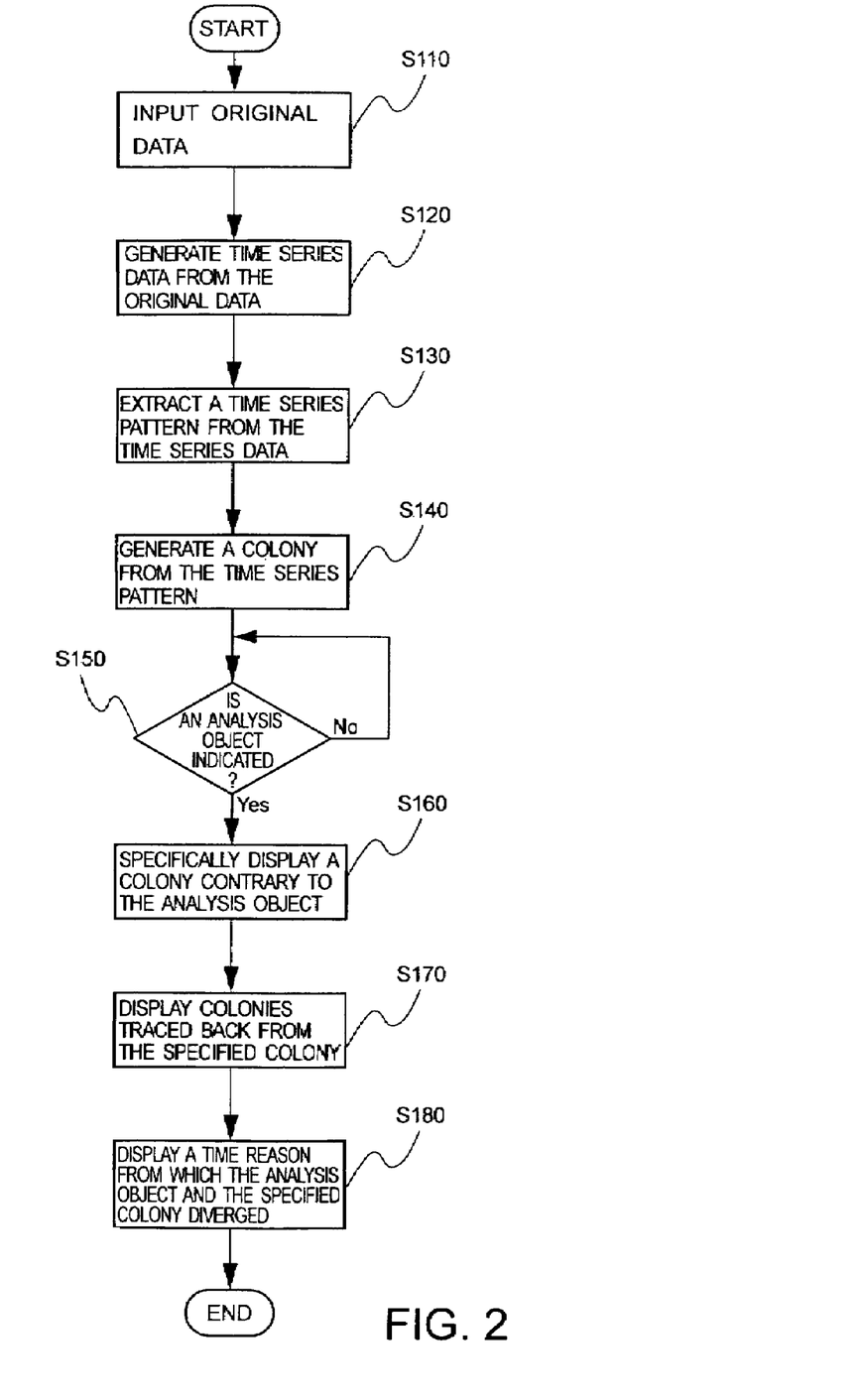
FIG. 2 is a flow chart of processing of the time series pattern extraction apparatus according to the first embodiment.

FIG. 1 is a block diagram of the time series pattern extraction apparatus 100 according to the first embodiment. FIG. 2 is a flow chart of processing of the time series pattern extraction apparatus 100 according to the first embodiment. As shown in FIG. 1, the time series pattern extraction apparatus 100 comprises an original data memory 110, an information extraction rule memory 120, a time series data generation unit 130, a time series data memory 140, a time series pattern extraction unit 150, a time series pattern memory 160, a colony generation unit 170, an input apparatus 180, and a display apparatus 190.

The original data memory 110 stores original data as a processing object. The original data is data including a date (For example, a sending time and date) such as an electronic mail. In the following explanation, the original data is a business daily report of an employee (such as a sales man). Briefly, the original data memory 110 is a database managed by a computer such as a server, and the employee updates a business daily report in the database through the computer (S110). The time series pattern extraction apparatus 100 executes a program shown in FIG. 2 to the original data uploaded in the database.

Figure 3:
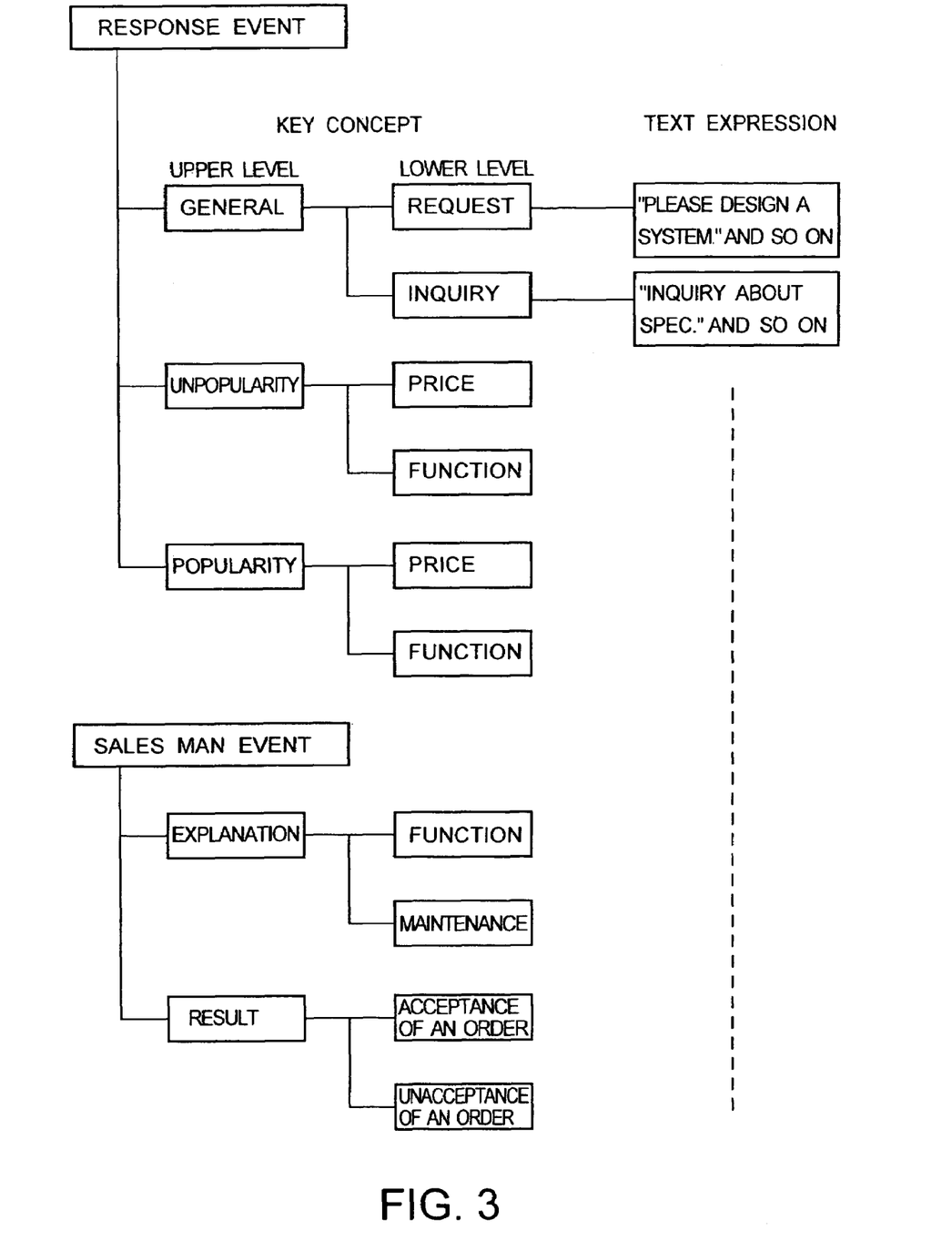
FIG. 3 is a schematic diagram of a tree structure of an information extraction rule memory 120 in FIG. 1.

FIG. 3 is a schematic diagram of a tree structure stored in the information extraction rule memory 120. For example, an information extraction rule comprises two parts "response event" and "sales man event". Upper level of a key concept in "response event" is "general", "unpopularity" and "popularity". Lower level of a key concept "general" is "request" and "inquiry". Lower level of a key concept "unpopularity" is "price" and "function". Lower level of a key concept "popularity" is "price" and "function".

On the other hand, upper level of a key concept in "sales man event" is "explanation" and "result". Lower level of a key concept "explanation" is "function" and "maintenance". Lower level of a key concept "result" is "acceptance of an order" and "unacceptance of an order".

As shown in FIG. 3, a correspondence relation table between key concepts and text expressions of original data is stored in the information extraction rule memory 120. For example, a key concept "general•request" and a text expression "Please design a system." Are linked or corresponded. Furthermore, a key concept "general•inquiry" and a text expression "Inquiry about spec." are corresponded. In case of original data "sales man A; business daily report of November 1; The customer told me, "please design a system."..", a time series event "sales man A; November 1; general•request" is created from the text expression "Please design a system" included in the original data.

The time series data generation unit 130 generates time series events from the original data (stored in the original data memory 110) using the information extraction rule (stored in the information extraction rule memory 120). Furthermore, the time series data generation unit 130 arranges the time series events in earlier order of date, and stores arranged events in the time series data memory 140 (S120). The time series event comprises an employee ID, a date, and a key concept (extracted from the original data). Time series data is a list (earlier order of date) of the time series events of each employee ID. Briefly, the time series event is an event of time series data occurred at some time.

Figure 4:
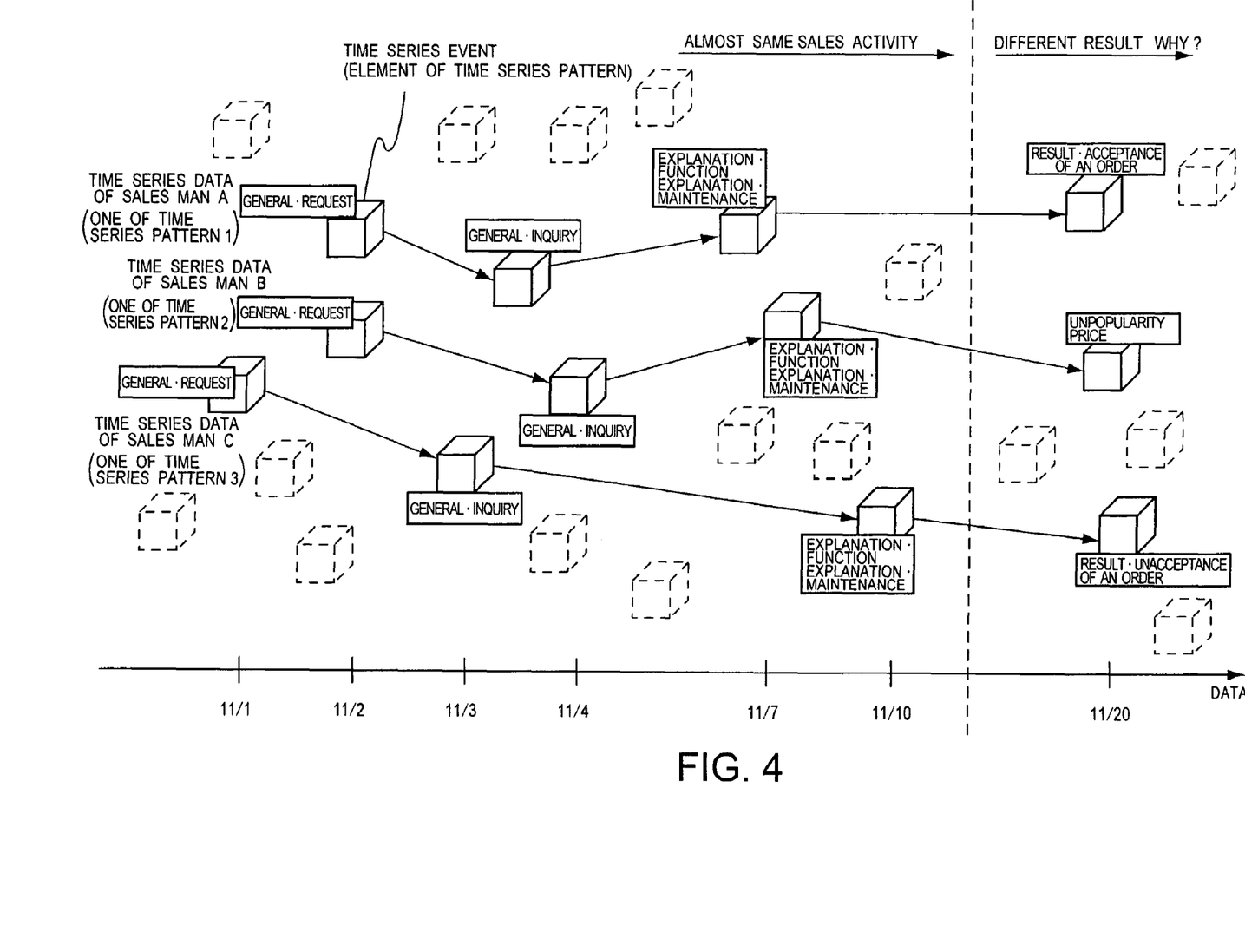
FIG. 4 is a schematic diagram of a plurality of time series data displayed over a passage of time.

FIG. 4 is a schematic diagram of the time series data on a display. Originally, the time series data is business daily reports of sales men (For example, several hundred persons) collected over a long term (For example, one year). In FIG. 4, in order to simplify the explanation, business daily reports of three sales men A, B, and C in November are displayed.

In FIG. 4, each time series event related with the information extraction rule "response event" or "sales man event" are represented as a cube of a solid line. Other time series events are represented as a cube of a dotted line. Furthermore, a status transition between two time series events is represented as an arrow. For example, a time series flow ("11/2; general•request"→"11/3; general•inquiry"→"11/7; explanation•function, explanation•maintenance"→"11/20; result•acceptance of an order") is included. Briefly, a time series flow ("A request to design a system is received in 11/2."→"An inquiry for spec. presented by sales man is received in 11/3"→"I explained function and maintenance of the system in 11/7"→"I accepted an order from the customer in 11/20") is extracted.

On the other hand, after the same time series flow ("11/2; general•request"→"11/4; general•inquiry"→"11/7; explanation•function, explanation•maintenance"), a different time series event "11/20; unpopularity•price", i.e., "The customer claimed for price in 11/20", also exists. Furthermore, after the same time series flow ("11/1; general•request"→"11/3; general•inquiry"→"11/10; explanation•function, explanation•maintenance"), a different time series event "11/20; result•unacceptance of an order", i.e., "I failed in acceptance of an order in 11/20", also exists.

Briefly, as shown in FIG. 4, after the same sales activity ("general•request"→"general•inquiry"→"explanation•function, explanation•maintenance") is executed, a sales man A accepts an order from he customer ("result•acceptance of an order") while a sales man C fails in acceptance of an order from the customer ("result•unacceptance of an order"). In this case, an analyst (user) cannot determine a reason why two contrary results are obtained.

Accordingly, in the present embodiment, the time series pattern memory 160 stores the passage of time between two time series events neighbored in time series order. Furthermore, in order for the user to easily present the contrary result, the colony generation unit 170 generates a colony from a plurality of time series patterns stored in the time series pattern memory 160. The colony means a receptacle to receive predetermined elements of a plurality f time series patterns.

First, the time series pattern extraction unit 150 excludes all classification data (For example, the employee ID) except for the date and the key concept from each time series event stored in the time series data memory 140, and executes an algorithm of apriori base to partial time series data (For example, from "general•request" to "result•acceptance of an order") each of which time series element is the date and the key concept. For example, in the partial time series data, the same key concept included in high frequency time series events is extracted with the date and stored as a time series pattern element in the time series pattern memory 160. The time series pattern element is each element divided by an arrow in the time series pattern of FIG. 4. Briefly, the time series pattern element comprises the key concept of high frequency time series events and a passage of time from a previous element.

Figure 5:
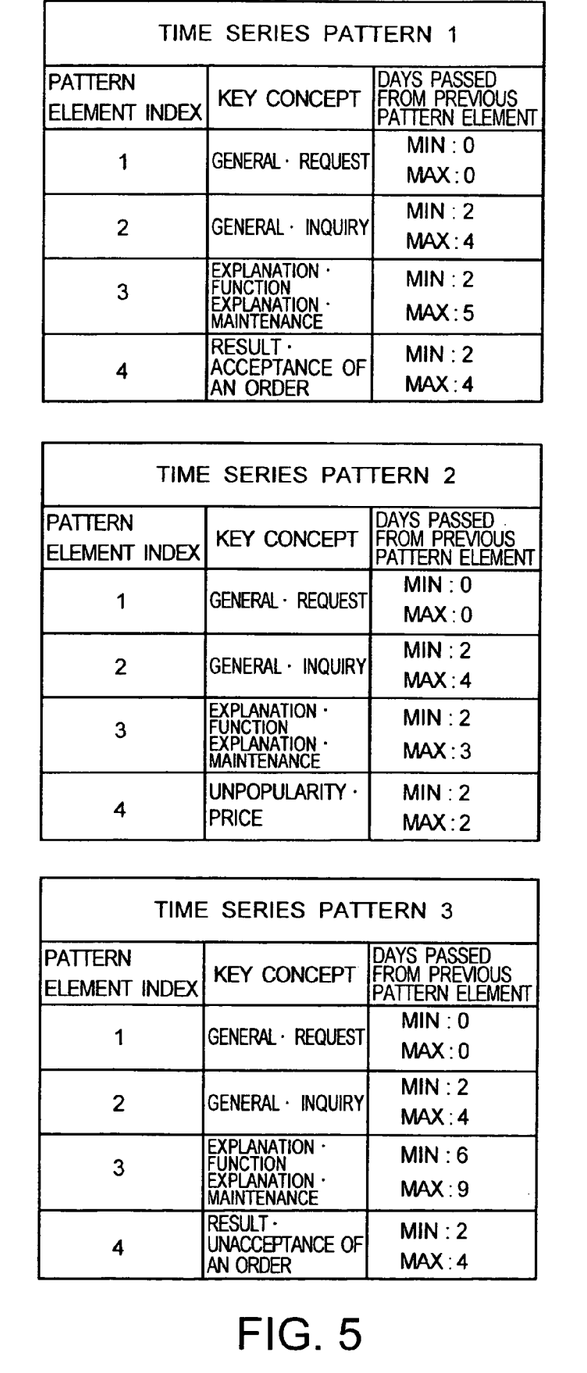
FIG. 5 is a schematic diagram of a data structure of a time series pattern memory 160 in FIG. 1.

In this case, the passage of time is a number of days passed from a previous element to the element. As shown in FIG. 5, minimum and maximum time durations of all time series pattern elements of the same key concept are stored in the time series pattern memory 160. For example, a time series pattern ("MIN=0, MAX=0; general•request"→"MIN=2, MAX=4; general•inquiry"→"MIN=2, MAX=5; explanation•function, explanation•maintenance"→"MIN=2, MAX=4; result•acceptance of an order") is stored (S130)

Figure 6:
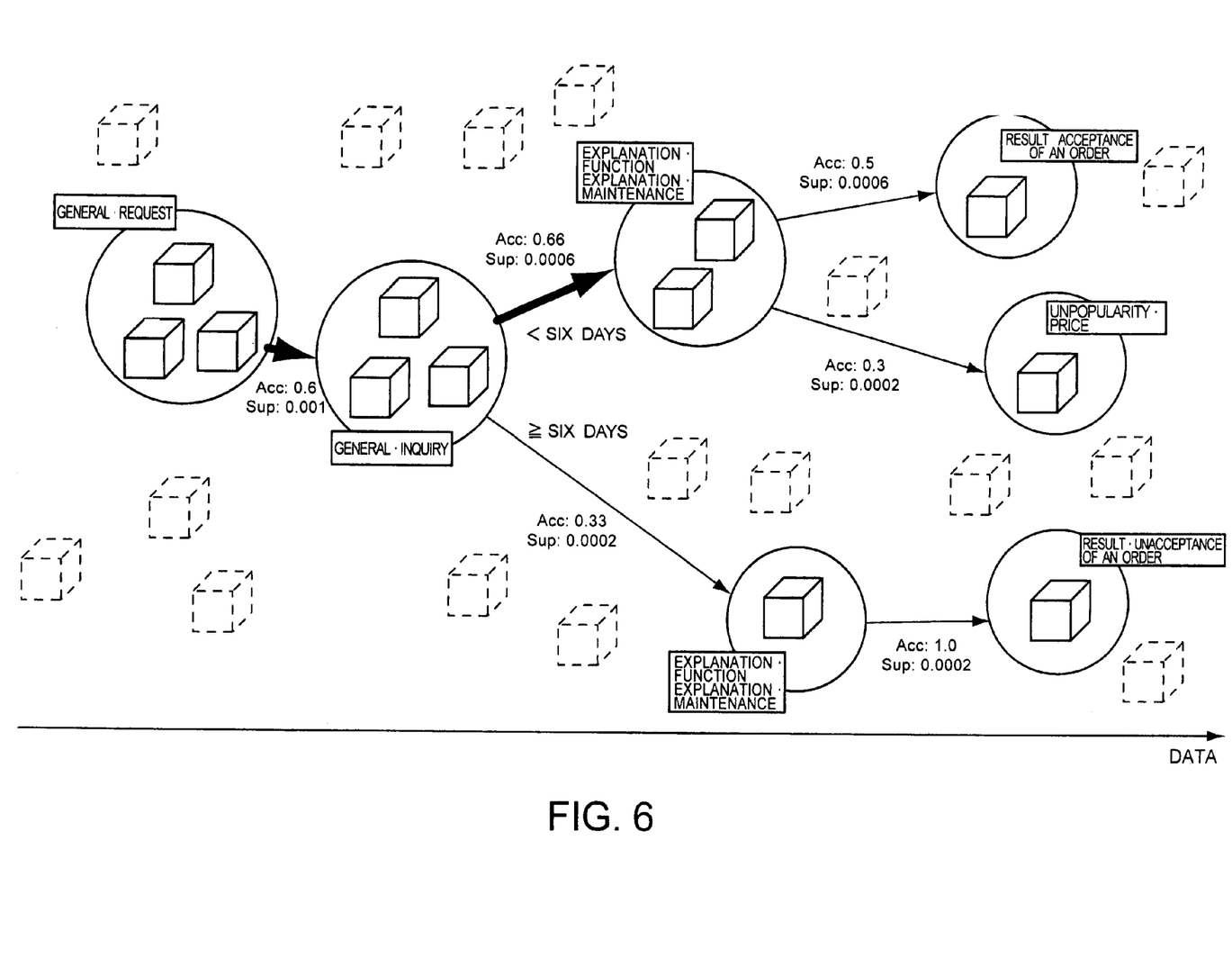
FIG. 6 is a schematic diagram of a plurality of colonies created from the time series patterns in FIG. 4.

The colony generation unit 170 unifies a plurality of time series pattern elements of which key concepts are the same and passages of time (MIN, MAX) are substantially the same as one colony (S140). FIG. 6 is a schematic diagram of a plurality of colonies unified from a plurality of time series patterns 1, 2, and 3 in FIG. 4. In this case, the same key concept means the same upper level and the same lower level in case that the key concept comprises an upper level and a lower level. Furthermore, the same passage of time means almost the same number of days passed from a previous time series pattern element. In FIG. 6, time series pattern elements "explanation•function, explanation•maintenance" each of which passage of time from a previous time series pattern element "general•request" is below six days belong to the same colony. However, time series pattern elements "explanation•function, explanation•maintenance" each of which passage of time from a previous time series pattern element "general•request" is equal to or above six days belong to another colony. A circle of a colony is set as a size in proportion to a number of time series pattern elements belonging to the colony.

A status transition-between two colonies neighbored in time series is represented by an arrow. In FIG. 6, "Acc:" means a probability that a source colony of an arrow changes to a destination colony of the arrow. "Sup:" means a support ratio of a time series pattern (a transition path supported by the arrow) from a start colony (In FIG. 6, "general•request") to the destination colony of the arrow in all time series patterns (all transition paths from the start colony to each colony). For example, a possibility (Acc:) that status of the time series pattern changes from a colony "general•inquiry" to a next colony "explanation•function, explanation•maintenance" below six days is 0.66. A support ratio (Sup:) that a status of time series pattern transits from the start colony "general•request" to the destination colony "explanation•function, explanation•maintenance" not below six days through the intermediate colony "general•inquiry" is 0.0006. In this case, a possibility (0.66) to change to a colony "explanation•function, explanation•maintenance" below six days is larger than a possibility (0.33) to change to a colony "explanation•function, explanation•maintenance" not below six days. Accordingly, an arrow to change to the colony "explanation•function, explanation•maintenance" below six days is thickly displayed.

Next, a user Indicates a key concept "result" to be analyzed using the input apparatus 180 such as a mouse or a keyboard (Yes at S150). In response to this indication, the colony generation unit 170 extracts two colonies "result•acceptance of an order" and "result•unacceptance of an order" as a lower level of the key concept "result" (S160). Continually, the colony generation unit 170 retroactively extracts other colonies related with the two colonies in the possibility and the support ratio. Briefly, the colony generation unit 170 traces back other colonies transited in the past from the two colonies, and displays the other colonies on the display apparatus 190 (S170). Last, when a colony from which the two colonies diverge is displayed, a time reason as a divergence condition is displayed (S180). In this case, the user can retroactively analyze a divergence point from which the two colonies "result•acceptance of an order" and "result•unacceptance of an order" occur.

Alternatively, the user may indicate a colony "result•acceptance of an order" to be analyzed using the input apparatus 180. In this case, the colony generation unit 170 extracts another colony "result•unacceptance of an order" contrary to the indicated colony "result•acceptance of an order" from all colonies In this way, the colony generation unit 170 may trace back other colonies transited in the past from these two colonies.

Furthermore, in FIG. 6, in case that passage of time from a colony "general•inquiry" to a next colony "explanation•function, explanation•maintenance" is below six days, a last colony "result•acceptance of an order" is obtained. Accordingly, "after receiving an inquiry of a system from the customer, you must explain function and maintenance of the system as soon as possible. If so, you probably receive an Order of the system from the customer." may be displayed as an advice to the user.

Furthermore, two colonies ("result•acceptance of an order" and "result•unacceptance of an order") related with the user's indicated key concept "result", and colonies transited in the past from the two colonies, may be displayed while other colonies are not displayed (or lightly displayed). Briefly, in order for the user to find the divergence point, colonies related with the user's indicated key concept are emphatically displayed.

Furthermore, in FIG. 6, in case of emphatically displaying a status transition to the user's target colony "result•acceptance of an order" only, other status transitions to another colony may be lightly displayed. Alternatively, the status transition to the user's target colony may be three-dimensionally displayed.

In the disclosed embodiments, the processing can be accomplished by a computer-executable program, and this program can be realized in a computer-readable memory device.

In the embodiments, the memory device, such as a magnetic disk, a flexible disk, a hard disk, an optical disk (CD-ROM, CD-R, DVD, and so on), an optical magnetic disk (MD and so on) can be used to store instructions for causing a processor or a computer to perform the processes described above.

Furthermore, based on an indication of the program installed from the memory device to the computer, OS (operation system) operating on the computer, or MW (middle ware software), such as database management software or network, may execute one part of each processing to realize the embodiments.

Furthermore, the memory device is not limited to a device independent from the computer. By downloading a program transmitted through a LAN or the Internet, a memory device in which the program is stored is included. Furthermore, the memory device is not limited to one. In the case that the processing of the embodiments is executed by a plurality of memory devices, a plurality of memory devices may be included in the memory device. The component of the device may be arbitrarily composed.

A computer may execute each processing stage of the embodiments according to the program stored in the memory device. The computer may be one apparatus such as a personal computer or a system in which a plurality of processing apparatuses are connected through a network. Furthermore, the computer is not limited to a personal computer. Those skilled in the art will appreciate that a computer includes a processing unit in an information processor, a microcomputer, and so on. In short, the equipment and the apparatus that can execute the functions in embodiments using the program are generally called the computer.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An apparatus for extracting a time series pattern, comprising:
    an input unit inputting a plurality of time series data, each time series data being an electronic daily report including a plurality of data elements, each data element including a time and a text;
    a data memory storing the plurality of time series data;
    an extraction rule memory storing a correspondence relation between a key concept and a text expression;
    a time series pattern generation unit configured to extract key concepts corresponding to the text of each data element of the plurality of time series data from said extraction rule memory, and to generate a plurality of time series patterns from the plurality of time series data, each pattern including data elements each having a time and a key concept;
    a colony generation unit configured to unify a plurality of data elements having the same key concept and substantially the same time duration, and to generate colonies of unified data elements;
    a select unit selecting a first colony from the colonies in response to a user's operation, the first colony having a first key concept;
    a colony extraction unit configured to specify a second colony having a second key concept contrary to the first key concept, and to extract colonies each having a time earlier than the first colony and the second colony;
    a time reason extraction unit configured to extract a time reason as a divergence condition of the first colony from the second colony from the extracted colonies; and
    a display unit displaying the first colony, the second colony, the extracted colonies, and the time reason.

2. The apparatus according to claim 1, wherein said extraction rule memory hierarchically stores the correspondence relation among an upper level key concept, a lower level key concept, and the text expression.

3. The apparatus according to claim 1, wherein said time series pattern generation unit replaces a text of each data element of the time to a series data with the key concept corresponding text expression included in the text, and generates the plurality of time series patterns in place of the plurality of time series data, each time series pattern including a plurality of data elements, each data element including the time and the key concept.

4. The apparatus according to claim 3, wherein said colony generation unit calculates a minimum and a maximum time duration between data elements having the same key concept and previous data elements having the same key concept, and unifies the data elements of the same key concept of which minimums and maximums are respectively equal as the same colony.

5. The apparatus according to claim 4, wherein said select unit selects the first colony of which key concept is an analysis object in response to the user's operation.

6. The apparatus according to claim 5, wherein said colony extraction unit traces other colonies in retroactive time series from the first colony or the second colony.

7. The apparatus according to claim 6, wherein said time reason extraction unit extracts a third colony from which the first colony and the second colony originally diverge from the other colonies, calculates a first time duration from the third colony to the first colony, calculates a second time duration from the third colony to the second colony, and generates the time reason based on a difference between the first time duration and the second time duration.

8. The apparatus according to claim 7, wherein said time reason extraction unit calculates a probability of transition from each colony to a next colony, and calculates a support ratio of transition from an origin colony to each colony in all transitions of the colonies, and wherein said display unit additionally displays the probability and the support ratio with an arrow between two colonies.

9. A method for extracting a time series pattern, comprising:
    inputting a plurality of time series data, each time series data being an electronic daily report including a plurality of data elements, each data element including a time and a text:
    storing the plurality of time series data in a data memory;
    storing a correspondence relation between a key concept and a text expression in an extraction rule memory;
    extracting key concepts corresponding to the text of each data element of the plurality of time series data from the extraction rule memory;
    generating a plurality of time series patterns from the plurality of time series data, each pattern including data elements each having a time and a key concept;
    unifying a plurality of data elements having the same key concept and substantially the same time durations;
    generating colonies of unified data elements;
    selecting a first colony from the colonies in response to a user's operation, the first colony having a first key concept;
    specifying a second colony having a second key concept contrary to the first key concept;
    extracting colonies each having a time earlier than the first colony and the second colony;
    extracting a time reason as a divergence condition of the first colony from the second colony from the extracted colonies; and
    displaying the first colony, the second colony, the extracted colonies, and the time reason.

10. The method according to claim 9, further comprising:
    hierarchically storing the correspondence relation among an upper level key concept, a lower level key concept, and the text expression in the extraction rule memory.

11. The method according to claim 9, at the first generating step, further comprising:
    replacing a text of each data element of the time series data with the key concept corresponding to a text expression included in the text; and
    generating the plurality of time series patterns in place of the plurality of time series data, each time series pattern including a plurality of data elements, each data element including the time and the key concept.

12. The method according to claim 11, at the unifying step, further comprising:
    calculating a minimum and a maximum time durations between data elements having the same key concept and previous data elements having the same key concept; and unifying the data elements of the same key concept of which minimums and maximums are respectively equal as the same colony.

13. The method according to claim 12, at the indicating step, further comprising:

selecting the first colony of which key concept is an analysis object in response to the user's operation.

14. The method according to claim 13, at the extracting step, further comprising:

tracing other colonies in retroactive time series from the first colony or the second colony.

15. The method according to claim 14, at the second extracting step, further comprising:

extracting a third colony from which the first colony and the second colony originally diverge from the other colonies;

calculating a first time duration from the third colony to the first colony;

calculating a second time duration from the third colony to the second colony; and generating the time reason based on a difference between the first time duration and the second time duration.

* * * * *